US008070793B2

(12) United States Patent  
Igaki (10) Patent No.: US 8,070,793 B2  
(45) Date of Patent: Dec. 6, 2011

(54) STENT FOR VESSEL

(75) Inventor: Keiji Igaki, Kyoto (JP)

(73) Assignee: Kabushikikaisha Igaki Iryo Sekkei, Kyoto (JP)

( * ) Notice: Subject to any disclaimer, the term of this patent is extended or adjusted under 35 U.S.C. 154(b) by 228 days.

(21) Appl. No.: 11/718,781

(22) PCT Filed: Nov. 11, 2005

(86) PCT No.: PCT/JP2005/020737  
§ 371 (c)(1), (2), (4) Date: Aug. 2, 2007

(87) PCT Pub. No.: WO2006/051912  
PCT Pub. Date: May 18, 2006

(65) Prior Publication Data  
US 2007/0282428 A1    Dec. 6, 2007

(30) Foreign Application Priority Data

Nov. 12, 2004    (JP) ............... P2004-329540

(51) Int. Cl.  
*A61F 2/06* (2006.01)
(52) U.S. Cl. .................. 623/1.15; 623/1.16
(58) Field of Classification Search ............ 623/1.15, 623/1.13, 1.12, 1.16  
See application file for complete search history.

(56) References Cited

U.S. PATENT DOCUMENTS

| 5,500,013 | A  | * | 3/1996  | Buscemi et al. ........... 623/1.22 |
| 5,935,162 | A  | * | 8/1999  | Dang ........................ 623/1.15 |
| 6,187,036 | B1 | * | 2/2001  | Shaolian et al. ........... 623/1.15 |
| 6,245,103 | B1 |   | 6/2001  | Stinson |
| 6,500,204 | B1 |   | 12/2002 | Igaki |
| 6,719,934 | B2 |   | 4/2004  | Stinson |
| 6,730,117 | B1 | * | 5/2004  | Tseng et al. ............... 623/1.16 |
| 2001/0010015 | A1 | * | 7/2001 | Hijlkema ................... 623/1.16 |

(Continued)

FOREIGN PATENT DOCUMENTS

EP    1 543 860 A1    6/2005

(Continued)

OTHER PUBLICATIONS

Written Opinion of the International Searching Authority for corresponding Application No. PCT/JP2005/020737 filed on Nov. 11, 2005.

(Continued)

*Primary Examiner* — Elizabeth Houston  
*Assistant Examiner* — Julie A Szpira  
(74) *Attorney, Agent, or Firm* — K&L Gates LLP (57) ABSTRACT

Disclosed is a stent for a vessel implanted and left in the vessel of a living body to support the lumen of the vessel from inside. The stent for a vessel consists of a plurality of stent constituting members (4a and 4b), formed by combining a plurality of the tubular-body constituting elements (5a and 5b) in multistage, each of the tubular-body forming elements (5) comprising a part of a tubular member (2) is formed by bending a yarn (3) of a biodegradable polymer in a zigzag design. Each of stent constituting members (4a and 4b) is comprised with tubular segments (6) formed by combining the tubular-body forming elements (5a and 5b) facing each other, and by continuously joining at least neighboring parts of each tubular-body forming element (5a and 5b) together, to comprise a continuously joined tubular body (2).

12 Claims, 8 Drawing Sheets

U.S. PATENT DOCUMENTS

| | | | |
|---|---|---|---|
| 2001/0021871 A1* | 9/2001 | Stinson | 623/1.15 |
| 2003/0088305 A1* | 5/2003 | Van Schie et al. | 623/1.12 |
| 2004/0127977 A1 | 7/2004 | Shanley | |
| 2006/0052859 A1* | 3/2006 | Igaki | 623/1.15 |

FOREIGN PATENT DOCUMENTS

| | | |
|---|---|---|
| JP | 11-57018 | 3/1999 |
| JP | 11-512306 | 10/1999 |
| JP | 2002-505146 | 2/2002 |
| JP | 2004-33579 | 2/2004 |
| JP | 2004-026174 | 4/2004 |
| JP | 2004-028615 | 4/2004 |
| JP | 2006-500121 | 5/2006 |
| WO | 92-15342 | 9/1992 |
| WO | 00-13737 | 3/2000 |
| WO | 2004/026174 A2 | 4/2004 |
| WO | 2004/028615 A1 | 8/2004 |

OTHER PUBLICATIONS

International Search Report dated Feb. 21, 2006 (2 pages).

* cited by examiner

STENT FOR VESSEL

TECHNICAL FIELD

This invention relates to a stent for a vessel implanted in a vessel of a living body, such as blood vessel, trachea or biliary, to support the lumen of the vessel from inside.

BACKGROUND ART

Heretofore, if a stenosis has occurred in a vessel of a living body, in particular the blood vessel, such as artery, a balloon forming portion provided in the vicinity of the distal end of a balloon catheter is inserted into this stenosis portion, and the wrapped balloon forming portion is inflated to expand the stenosis portion of the blood vessel to improve the blood flow in the vessel. This operation is termed percutaneous transluminal angioplasty (PTA).

However it has been known, if the PTA is applied, stenosis tends to be reproduced at a high probability in the once stenosis portion.

To prevent this restenosis, the technique of implanting a tubular stent in the site applied PTA has been used. This stent is inserted into the blood vessel as it is contracted in diameter, and subsequently expanded so as to be implanted in the blood vessel to support the blood vessel wall from its inside, and to prevent occurrence of restenosis in the blood vessel.

As such sort of the stent, a stent comprised a tubular metal member provided with an incision to permit its expansion or contraction in diameter has been known.

Metal stent may cause a reaction against a foreign substance by remaining for a prolonged time in a living body. Hence, it is not desirable or proper to remain metal stent in the living body semi-permanently. Moreover, surgical operations are needed to remove the metal stent once the stent is implanted in the living body, thus imposing a severe load on the patient.

To solve such inherent problem with the metal stent, the present inventor has proposed a stent formed of a biodegradable polymer in Patent Publications of WO92/15342 and WO00/13737. A stent formed of a biodegradable polymer has also been proposed in JP Laid-Open Patent Publication H-11-57018.

Recently, many reports have been made on the effect of a so-called drug eluting stent, which a drug is locally released from a stent implanted in the living body to restrain hyperplasia of neointima. The present inventor has proposed in the Publication of WO2004/028615 a so-called drug eluting stent in which a drug is locally released from to restrain hyperplasia of neointima.

DISCLOSURE OF THE INVENTION

Problem to be Solved by the Invention

Meanwhile, it is desired for a stent implanted in a vessel of a living body such as blood vessel to have flexibility to be deformed easily in sinuous or meandering vessel, in order to be inserted smoothly into the vessel.

It is also desired for a stent to have sufficient force to reliably support the inner wall of the vessel expanded state in order to permit circulation of the body fluid such as blood within the vessel when the stent is implanted in the vessel, such as blood vessel.

It is moreover desired for a stent for a vessel in expanded state to support entire circumference of the inner wall of the vessel with a uniform force so as to be implanted in the vessel without injuring the inner wall of the vessel.

It is an object of the present invention to provide a stent for a vessel which has advantage property of the biodegradable polymer and which is able to realize the properties required for the stent for a vessel implanted in the vessel.

It is another object of the present invention to provide a stent for a vessel which is formed of a biodegradable polymer and superior in flexibility, and which is able to support the inner wall of the stenosis vessel such as blood vessel with sufficient supporting strength, and expand and support the inner wall of the vessel with a uniform force.

It is a further object of the present invention to provide a stent for a vessel with superior in productivity.

It is yet another object of the present invention to provide a stent for a vessel, which is able to release drug into the living body.

The stent for a vessel according to the present invention is comprised with a tubular body formed by comprising a plural number of stent constituting members formed of yarns of a biodegradable polymer.

Each stent constituting member making up the tubular body is constituted by a plural number of tubular-body forming elements.

Individual tubular-body forming element is formed by bending a yarn of a biodegradable polymer, which forms the stent constituting member, in a zigzag design. A plural number of the tubular-body forming elements are combined in multistage at each connecting parts of yarns of the same material of a biodegradable polymer.

The stent constituting members made up by a plural number of the tubular-body forming elements, combined at the connecting parts in multistage are placed adjacently to one another, and are at least partly joined and combined the tubular-body forming elements together to form a single tubular body.

Individual stent constituting members are unified together by joining the neighboring sides or bends apices of the yarn bent in a zigzag design.

The neighboring tubular-body forming elements are joined together by an adhesive, or by dissolving part of the yarn with a solvent to dissolve the biodegradable polymer that makes up the yarn. Joining may also be done by a solution obtained on dissolving the biodegradable polymer with a solvent, or done by dissolving part of the yarn with the energy of laser light.

The tubular-body forming elements constitute a plural number of tubular segments by unified together by joining at least part of each element. These tubular segments constitute the continuous tubular body by combining in multistage with the connecting parts to combine each tubular-body forming elements to generate.

The connecting parts to combine the tubular segments are staggered from one stage to the next.

The tubular body constituting the stent for a vessel according to the present invention has the connecting parts of tubular segments as displacing portions to be flexed.

The tubular body may also be contracted or expanded in diameter with bends of the yarn bent in a zigzag design as displacing portions.

The yarn constituting the stent constituting member is a non-interrupted continuous monofilament. The yarn may be a multifilament made up of plural monofilaments unified together.

The yarn is formed of one or more of biodegradable polymers from among polylactic acid (PLLA), polyglycolic acid (PGA), a copolymer of polyglycolic acid and polylactic acid, polydioxanone, a copolymer of trimethylene carbonate and glycolid and a copolymer of polyglycolic acid or polylactic acid and ε-caprolactone.

A plural number of the stent constituting members may be formed by yarns each made of different sorts of the biodegradable polymers.

The stent for a vessel according to the present invention may also contain a drug.

The stent for a vessel according to the present invention is constituted by combining a plural number of the stent constituting members having the tubular-body forming element constituting part of the tubular body formed by bending a yarn of biodegradable polymer in a zigzag design, and then because at least part of the neighboring portions of each tubular-body forming element are joined. The strength of the tubular segment comprised by combining the tubular-body forming elements may be assured, and the tubular body may be kept in the stabile form. Hence the stent has sufficient strength to reliably support the inner wall of the vessel as it is expanded in diameter.

The stent for a vessel according to the present invention is a tubular body comprised by combining plural stent constituting members, and may be flexed along its length with the connecting parts combining the tubular-body forming elements of the stent constituting members in multistage as displacing portions. Hence, the stent for a vessel according to the present invention is flexible to be deformed easily in the sinuous vessel.

The connecting parts combining each connecting parts of the stent constituting member for joining the tubular-body forming elements in multistage, in the stent constituting member, are staggered along the circumference of the tubular body. Hence, the stent for a vessel composed of the tubular body comprised by combining plural stent constituting members has uniform strength circumferentially.

In addition, the stent for a vessel, composed of the tubular body has plural connecting parts for combining the tubular segments in multistage, and hence is able to support the inner wall in the sinuous vessel in the expanded state with a uniform force.

In addition, since the tubular body is formed by combining plural stent constituting members having the tubular-body forming elements comprising part of a tubular body, the stent for a vessel may be manufactured with ease and is superior in mass-producibility.

Furthermore, by containing a drug, the stent for a vessel has the function of a so-called drug eluting stent and is able to administer a drug reliably to a desired location in the living body.

Other objects and advantages derived of the present invention will become more apparent from the following preferred embodiment which is described with reference to the accompanying drawings.

BEST MODE FOR CARRYING OUT THE INVENTION

Referring to the drawings, the preferred embodiment of a stent for a vessel according to the present invention is described in detail.

Figure 1:
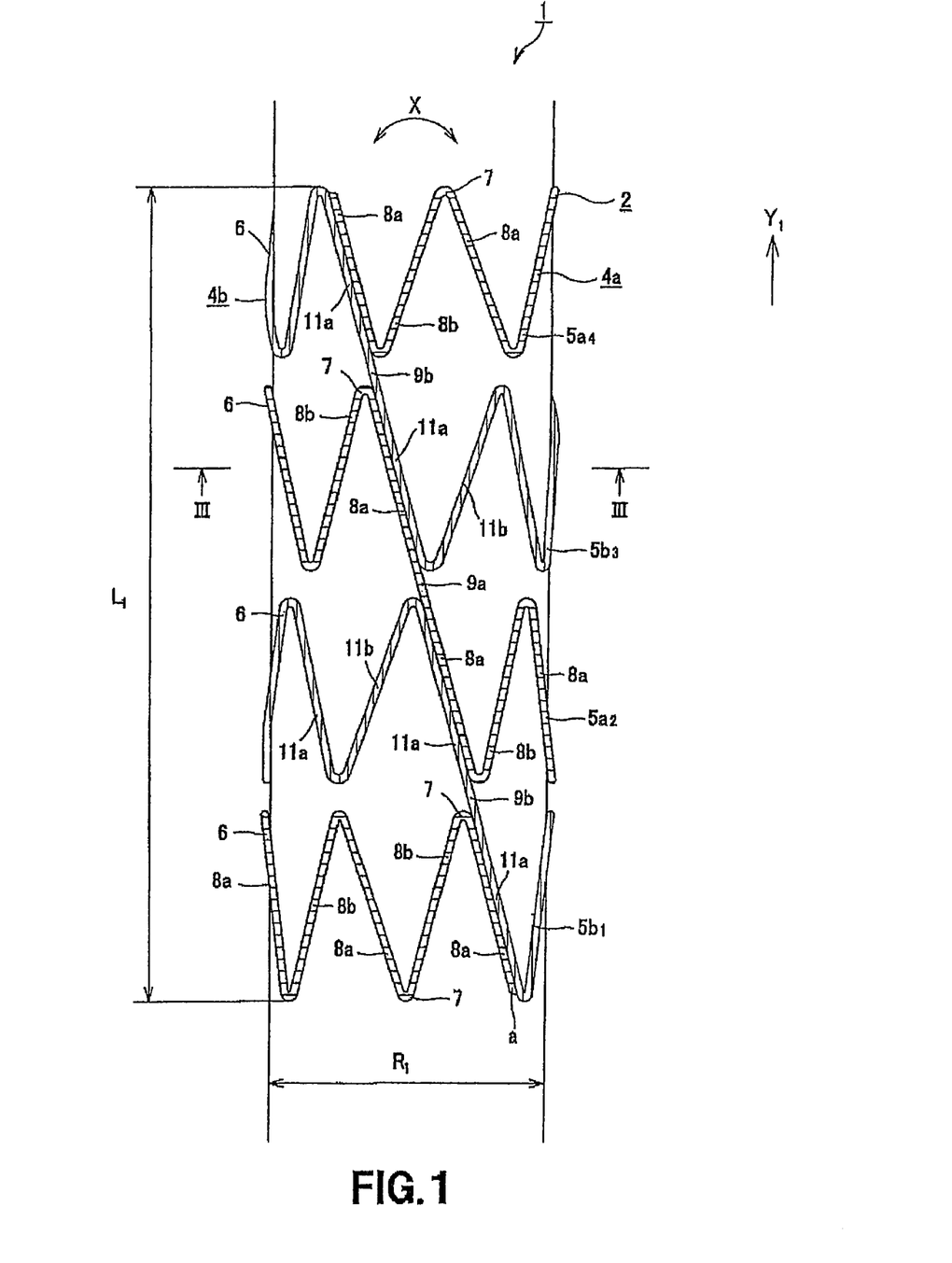
FIG. 1 is a side view showing one side of a stent for a vessel according to the present invention.
Figure 2:
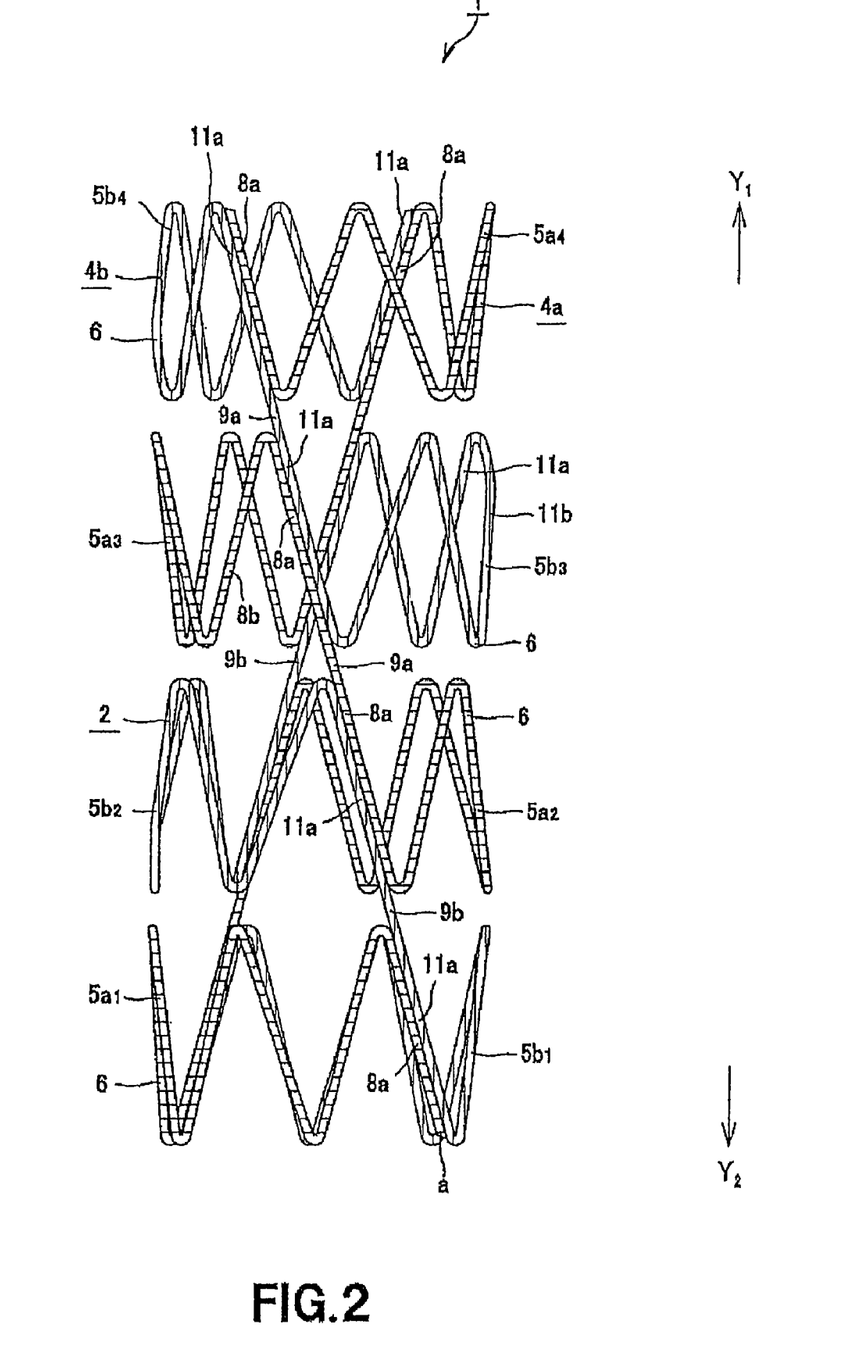
FIG. 2 is a perspective view showing a stent for a vessel according to the present invention.
Figure 3:
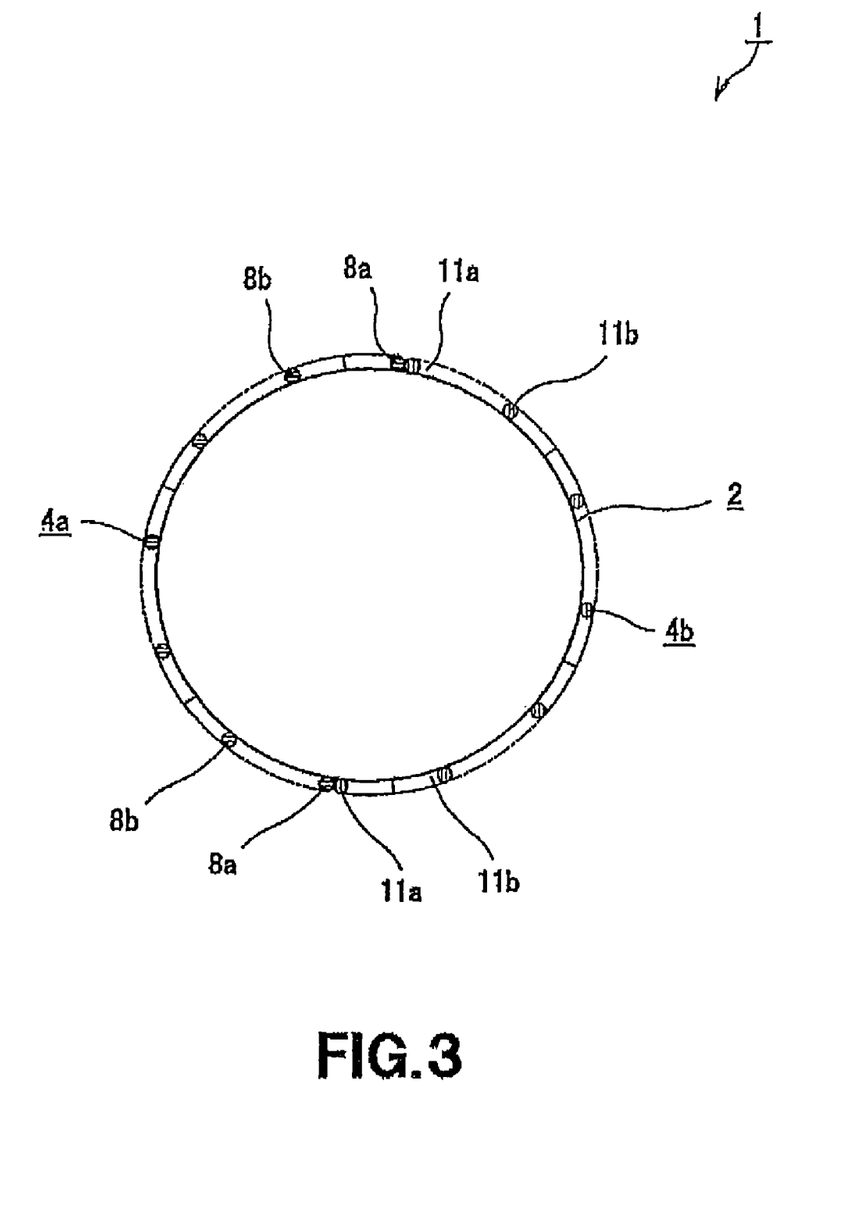
FIG. 3 is a cross-sectional view of the stent for a vessel, taken along line III-III of FIG. 1.

A stent for a vessel 1 according to the present invention is used as it is implanted in a blood vessel, such as a coronary artery of a living body, and is comprised with tubular body 2 of cylindrical shape, as shown in FIGS. 1 to 3.

FIG. 1 is a side view showing one-way semi-cylindrical part of the tubular body 2 formed cylindrically. FIG. 2 is a perspective view of the entire tubular body 2 and FIG. 3 is a cross-sectional view taken along line III-III of FIG. 1.

The stent for a vessel 1 implanted in the blood vessel is made with outer diameter $R_1$ of 3 to 5 mm and length $L_1$ of 10 to 15 mm. This size is the one when the stent is implanted in the blood vessel of the living body.

Meanwhile, the size of the stent for a vessel 1 is selected as appropriate depending on the vessel in which the stent is implanted.

The stent for a vessel 1 according to the present invention consists of the cylindrical tubular body 2 combined plural stent constituting members 4a and 4b formed of a biodegradable polymer yarn.

The yarn 3 is formed of a biodegradable polymer which, when implanted in the living body such as human body, does not affect the living body. The biodegradable polymer may be polylactic acid (PLLA), polyglycolic acid (PGA), polyglactin (copolymer of polyglycolic acid and polylactic acid), polydioxanone, polyglyconate (copolymer of trimethylene carbonate and glycolid), or a copolymer of polyglycolic acid or polylactic acid and ε-caprolactone. It is also possible to use biodegradable polymers obtained on compounding two or more of these materials.

Figure 4:
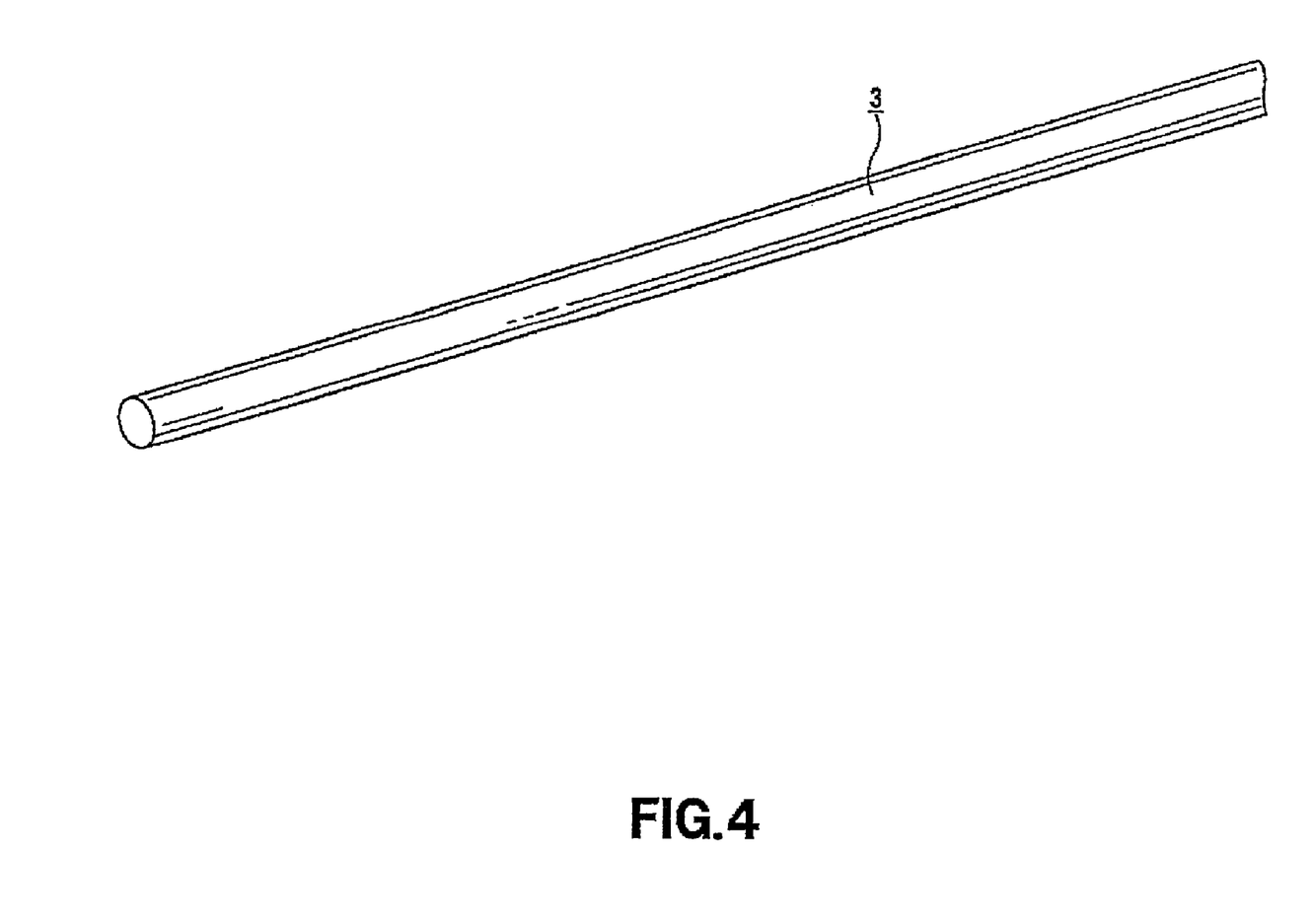
FIG. 4 is a perspective view showing a yarn to form a stent constituting member.
Figure 5:
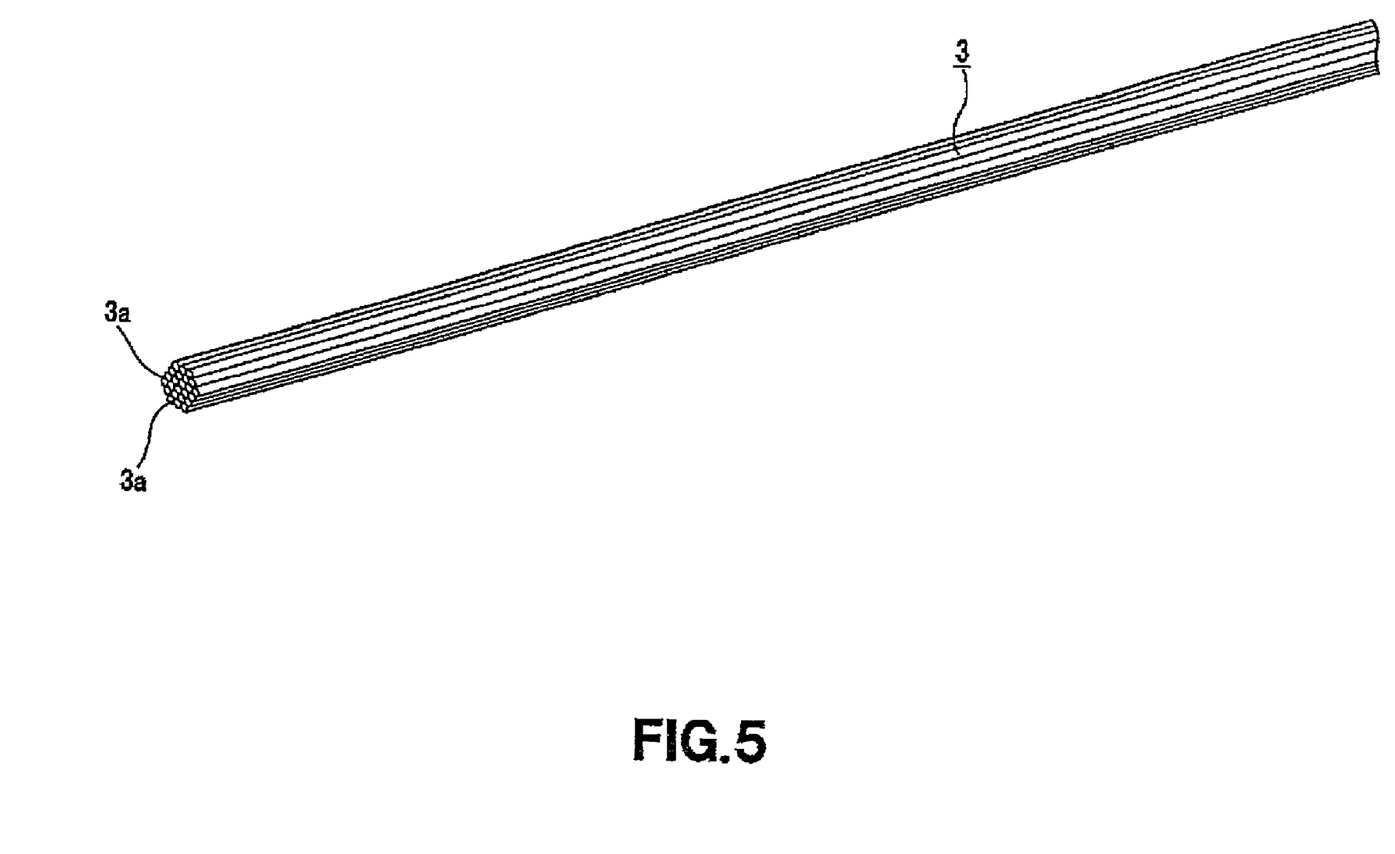
FIG. 5 is a perspective view showing another example of a yarn to form a stent constituting member.

The yarn 3 may be used a monofilament composed of a continuous biodegradable polymer, as shown in FIG. 4, or a multifilament composed of a plural number of monofilaments 3a, unified together, as shown in FIG. 5.

Meanwhile, the monofilament and the multifilament may be formed by melt-spinning a biodegradable polymer with a melt spinning device.

In the present embodiment, the tubular body 2 is formed by combining a pair of stent constituting members 4a and 4b, as shown in FIGS. 1 to 3. These stent constituting members 4a and 4b are each formed by a single yarn 3.

Each stent constituting member 4a and 4b has the tubular-body forming elements 5a and 5B each formed by bending a single yarn 3 in a zigzag design. The tubular-body forming elements 5a and 5b forming the stent constituting members 4a and 4b, respectively, are combined together to constitute a cylindrical tubular segments 6, as shown in FIGS. 2 and 3. The tubular segment 6 comprises a part of the continuous tubular body 2, as shown in FIGS. 1 and 2. That is, the tubular body 2 is made up by combining the tubular segments 6 in multistage form, as shown in FIGS. 2 and 3.

A pair of the stent constituting members 4a and 4b making up the tubular body 2 are now explained in detail.

Figure 6:
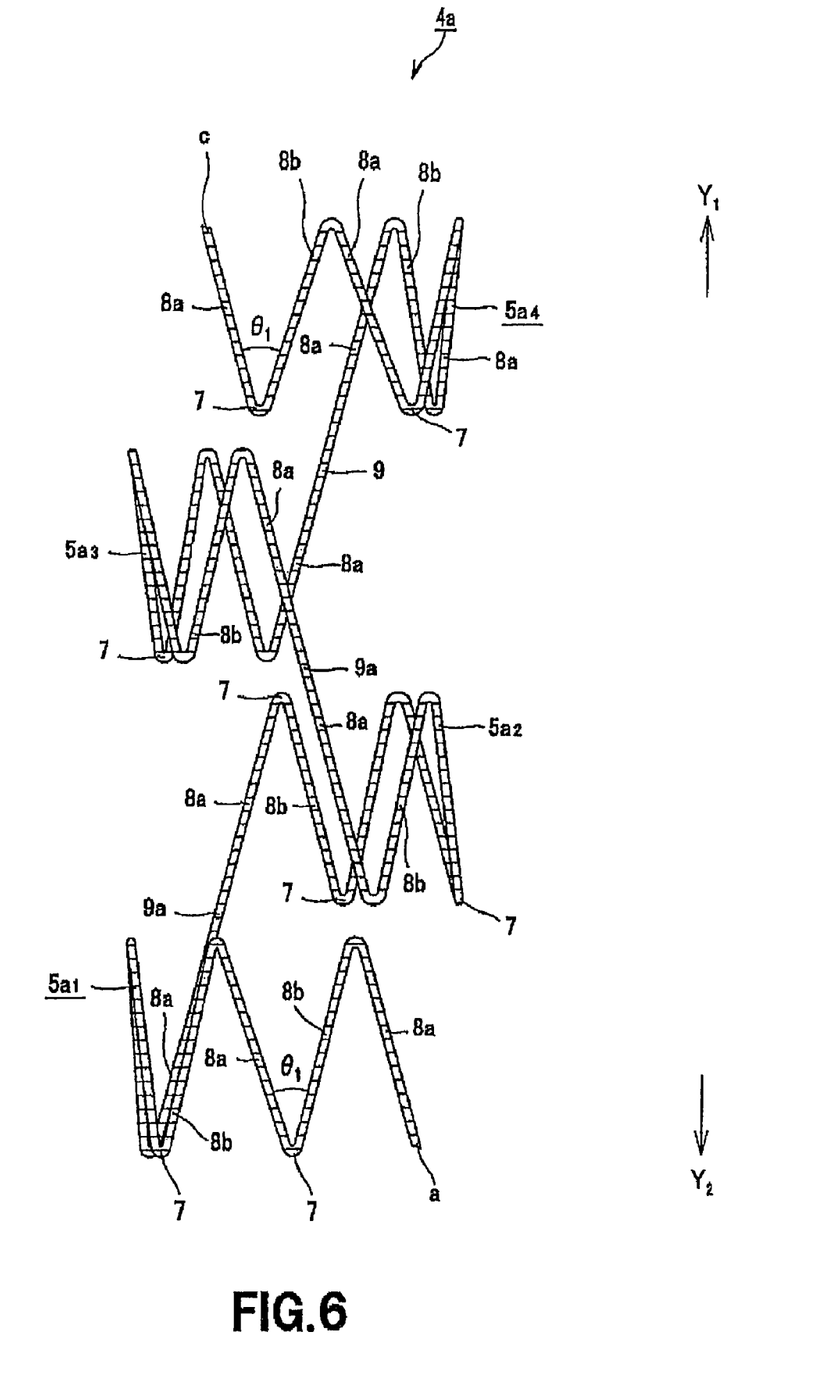
FIG. 6 is a perspective view showing one of the stent constituting members constituting a stent for a vessel according to the present invention.

First, the stent constituting member 4a is explained. This stent constituting member 4a is formed by bending the single yarn 3 as shown in FIG. 6. The yarn 3 making up the stent constituting member 4a is, for example, bent in a zigzag design from the starting point "a" shown at the lower right end of FIG. 6. Initially, the yarn 3 is bent so that the bend 7 protrudes toward the direction of arrow $Y_1$ in FIG. 6. The yarn is then bent so that the bend 7 protrudes toward the direction of arrow $Y_2$ in FIG. 6. The yarn 3 is bent in a zigzag design in succession for plural times so that the directions of protrusion of the bends 7 are reversed in turn. This completes a single tubular-body forming element 5a.

The tubular-body forming element 5a, thus obtained, is curved in a semi-cylindrical shape to constitute portion of the tubular segment 6 (see FIGS. 3 and 6).

The yarn 3 bent to form a tubular-body forming element 5a is bent so that a pair of left and right sides 8a and 8b positioned both sides from the bend 7 in between are approximately the same length. A pair of sides 8a and 8b formed by bending the yarn 3 in V shape or U shape, with the bend 7 in between may displace, with the bend 7 as displacing portions by having an angle $\theta_1$ defined between these sides 8a and 8b larger or smaller.

The yarn 3 is bent in a zigzag design even times to form a single tubular-body forming element 5a. The tubular-body forming element 5a is formed by bending the yarn 3 even times, so that when the bend 7 protruding upwards to the direction of arrow $Y_1$ in FIG. 6 is at the sides of the starting point "a" of bending, the bend 7 protruding downward to the direction of arrow $Y_2$ in FIG. 6 is at the ending point of the opposite side, that is, at a terminal end of bending. As a result, the yarn 3 is able to be extended at the terminal end of bending in an upward direction of arrow $Y_1$ in FIG. 6.

The yarn 3 extended toward the direction of arrow $Y_1$ in FIG. 6 from a tubular-body forming element $5_{a1}$ of the first bottom stage in FIG. 6 is bent in a zigzag design, with the connecting part 9a from the tubular-body forming element $5_{a1}$ of the first stage as a starting point of bending, to form the tubular-body forming element $5_{a2}$ of a second stage. The tubular-body forming element $5_{a2}$ of the second stage is bent not to overlap the bends 7 protruding downwards to the direction of arrow $Y_2$ in FIG. 6 and the bends 7 of the tubular-body forming element $5_{a1}$ of the first stage protruding upwards to the direction of arrow $Y_1$ in FIG. 6.

That is, the tubular-body forming element $5_{a2}$ of the second stage is bent in such a way that there is a slight space between apices the bends 7 thereof and the bends 7 of the first tubular-body forming element $5_{a1}$, or that the two bends simply touch each other without overlapping.

The tubular-body forming element $5_{a2}$ of the second stage is also formed by bending the yarn 3 even times.

The tubular-body forming element $5_{a2}$ of the second stage is formed so as to be placed in the opposite position staggered by approximately 180° from the tubular-body forming element $5_{a1}$ of the first stage.

The yarn 3 extended upwards to the direction of arrow $Y_1$ in FIG. 6 from the tubular-body forming element $5_{a2}$ of the second stage is bent in a zigzag design even times, with the connecting part 9a from the tubular-body forming element $5_{a2}$ of the second stage as a starting point of bending, to form the tubular-body forming element $5_{a3}$ of the third stage. At this time, the tubular-body forming element $5_{a3}$ of the third stage is bent not to overlap the apices of the bends 7 thereof protruding downwards to the direction of arrow $Y_2$ in FIG. 6 and the apices of the bends 7 of the second tubular-body forming element $5_{a2}$ protruding upwards to the direction of arrow $Y_1$ in FIG. 6.

The tubular-body forming element $5_{a3}$ of the third stage is formed as it is staggered by approximately 180° from the tubular-body forming element $5_{a2}$ of the second stage, so that the tubular-body forming element $5_{a3}$ of the third stage is located at the side of the tubular-body forming element $5_{a1}$ of the first stage, and at the opposite side of the tubular-body forming element $5_{a2}$ of the second stage.

Moreover, the yarn 3 extended upwards to the direction of arrow $Y_1$ in FIG. 6 from the tubular-body forming element $5_{a3}$ of the third stage is bent in a zigzag design even times, with a connecting part 9a from the tubular-body forming element $5_{a3}$ of the third stage as a starting point of bending, to form the tubular-body forming element $5_{a4}$ of the fourth stage. At this time, the tubular-body forming element $5_{a4}$ of the fourth stage is also bent not to overlap the apices of the bends 7 protruding downwards to the direction of arrow $Y_2$ in FIG. 6 and the apices of the bends 7 of the third tubular-body forming element $5_{a3}$ protruding upwards to the direction of arrow $Y_1$ in FIG. 6.

The tubular-body forming element $5_{a4}$ of the fourth stage is formed as it is staggered by approximately 180° from the tubular-body forming element $5_{a3}$ of the third stage, that is, so that the tubular-body forming element $5_{a4}$ of the fourth stage is located at the side of the tubular-body forming element $5_{a2}$ of the second stage, and at the opposite side of the tubular-body forming element $5_{a3}$ of the third stage.

In this manner, the stent constituting member 4a is formed by combining a plural number of the tubular-body forming elements 5a in multistage via connecting parts 9a. Each tubular-body forming elements 5a are combined continuously via connecting parts 9a to face each other with the positions at respective stage staggered alternately by approximately 180°.

Figure 7:
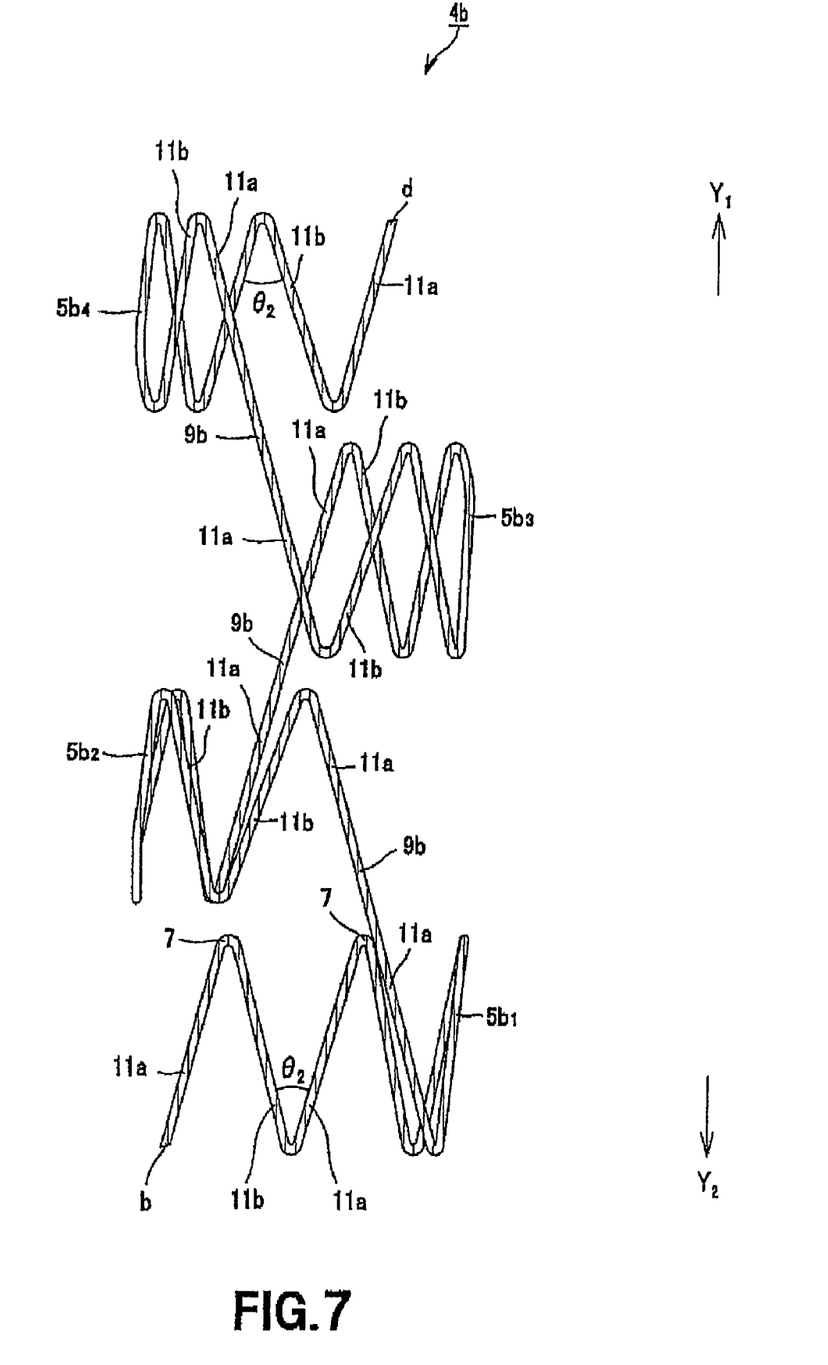
FIG. 7 is a perspective view showing the other stent constituting member constituting a stent for a vessel according to the present invention.

In the same manner as the stent constituting member 4a, the other stent constituting member 4b is also formed by bending the yarn 3 as shown in FIG. 7. The yarn 3 making up the other stent constituting member 4b is, for example, bent in a zigzag design, from the starting point "b" shown at the left end of FIG. 7. Initially, the yarn 3 is bent so that the bend 7 protrudes upwards to the direction of arrow $Y_1$ in FIG. 7. The yarn is then bent so that the bend 7 protrudes downwards to the direction of arrow $Y_2$ in FIG. 7. The yarn 3 is then bent in a zigzag design in succession for plural times so that the direction of protrusion of the bends 7 are reversed in turn. This completes a single tubular-body forming element 5b.

The yarn 3, bent to form a tubular-body forming element 5b, is also bent so that a pair of left and right sides 11a and 11b positioned both sides from the bend 7 in between are approximately the same length. A pair of sides 11a and 11b formed by bending the yarn 3 in V shape with the bend 7 in between may displace, in the same manner as the foresaid stent constituting member 4a, with the bend 7 as displacing positions by having an angle $\theta_2$ defined between these sides 11a and 11b larger or smaller.

The yarn 3 is, in the same manner as the stent constituting member 4a, bent in a zigzag design even times to form a tubular-body forming element 5b. The tubular-body forming element 5b is as well formed by bending the yarn 3 even times, so that when the bend 7 protruding upwards to the direction of arrow $Y_1$ in FIG. 7 is at the side of the starting point "b" of bending, the bend 7 protruding downwards to the direction of arrow $Y_2$ in FIG. 7 is at the ending point of the opposite side, that is, at a terminal end of bending. As a result, the yarn 3 is extended at the terminal end of bending toward the direction of arrow $Y_1$ in FIG. 7.

The yarn 3 extended upwards to the direction of arrow $Y_1$ in FIG. 7 from a tubular-body forming element $5_{b1}$ of the first bottom stage in FIG. 7 is bent in a zigzag design with a connecting part 9b from the tubular-body forming element $5_{b1}$ of the first stage as a starting point of bending, to form the tubular-body forming element $5_{b2}$ of a second stage. The tubular-body forming element $5_{b2}$ of the second stage is bent not to overlap the bends 7 protruding downwards to the direction of arrow $Y_2$ in FIG. 7 and the bends 7 of the tubular-body forming element $5_{b1}$ of the first stage protruding upwards to the direction of arrow $Y_1$ in FIG. 7, in the same manner as said stent constituting member 4a.

In the same manner as the tubular-body forming element 5a provided in the stent constituting member 4a described above, the tubular-body forming element $5_{b3}$ of the third stage is formed by bending the yarn 3 extending from the tubular-body forming element $5_{b2}$ of the second stage while the tubular-body forming element $5_{b4}$ of the fourth stage is formed by bending the yarn 3 extending from the tubular-body forming element $5_{b3}$ of the third stage in a zigzag design. Since the method of forming those tubular-body forming elements and the structure thereof are same as those of the tubular-body forming element 5a provided for the stent constituting member 4a, detailed description therefore is omitted.

The paired stent constituting members 4a and 4b are formed by folding the yarn 3 in a zigzag design with the starting points a and b in opposition to each other in the left-and-right, as shown in FIGS. 6 and 7, and hence are configured symmetrically in left-and-right direction. The paired stent constituting members 4a and 4b are formed with the common number, size and the shape of the tubular-body forming elements 5a and 5b. The tubular-body forming elements 5a and 5b are formed congruently with common length of the sides 8a and 8b, and the sides 11a and 11b, and the common number of bending time of the yarn 3.

The paired stent constituting members 4a and 4b constructed as described above are abutted against each other with the tubular-body forming elements 5a and 5b facing each other to constitute the single tubular body 2.

As shown FIG. 2, the sides 8a lying on the side of the starting point "a" of bending of the tubular-body forming element $5_{a1}$ of the first stage, comprising the stent constituting member 4a is abutted in parallel with the side 11a lying on the connecting part 9b to the tubular-body forming element $5_{b2}$ of the second stage, viz. lying on the side of the terminal point of bending of the tubular-body forming element $5_{b1}$ of the first stage of the other stent constituting member 4b. The side 8a lying on the connecting part 9a to the tubular-body forming element $5_{a2}$ of the second stage, viz. lying on the side of the terminal point of bending of the tubular-body forming element $5_{a1}$ of the first stage comprising the stent constituting member 4a, is abutted in parallel with the side 11a on the side of the starting point "b" of bending of the tubular-body forming element $5_{b1}$ of the first stage comprising the other stent constituting member 4b.

Similarly, in the tubular-body forming elements $5_{a2}$, $5_{b2}$, $5_{a3}$ and $5_{b3}$ of the second and third stage, the side 8a lying on the side of the starting point of bending of the tubular-body forming element $5_{a2}$ of the second stage of the stent constituting member 4a is abutted in parallel with the side 11a lying on the connecting part 9b to the tubular-body forming element $5_{b3}$ of the third stage, viz. lying on the side of the terminal point of bending of the tubular-body forming element $5_{b2}$ of the second stage of the other stent constituting member 4b, while the side 8a on the side of the starting point of bending of the tubular-body forming element $5_{a3}$ of the third stage of the stent constituting member 4a is abutted in parallel with the side 11a lying on the connecting part 9b to the tubular-body forming element $5_{b1}$ of the first stage, viz. lying on the side of the terminal point of bending of the tubular-body forming element $5_{b3}$ of the first stage of the other stent constituting member 4b. The side 8a lying on the connecting part 9a to the tubular-body forming element $5_{a3}$ of the third stage, viz. lying on the side of terminal point of bending of the tubular-body forming element $5_{a2}$ of the second stage comprising the stent constituting member 4a is abutted in parallel with the side 11a lying on the side of the starting point of bending of the tubular-body forming element $5_{b2}$ of the second stage comprising the other stent constituting member 4b, while the side 8a lying on the connecting part to the tubular-body forming element $5_{a4}$ of the forth stage, viz, lying on the side of terminal point of bending of the tubular-body forming element $5_{a3}$ of the third stage comprising the stent constituting member 4a is abutted in parallel with the side 11a lying on the side of the starting point of bending of the tubular-body forming element $5_{b3}$ of the third stage comprising the other stent constituting member 4b.

As for the tubular-body forming elements $5_{a4}$ and $5_{b4}$ of the fourth stage, the side 8a on the side of the starting point of bending of the tubular-body forming element $5_{a4}$ of the fourth stage comprising the stent constituting member 4a is abutted in parallel with the side 11a lying on the side of the terminal point "d" of bending of the tubular-body forming element $5_{b4}$ of the fourth stage of the other stent constituting member 4b. The side 8a on the side of the terminal point "c" of bending of the tubular-body forming element $5_{a4}$ of the fourth stage comprising the stent constituting member 4a is abutted in parallel with the side 11a on the side of the starting point of bending of the tubular-body forming element $5_{b4}$ of the fourth stage comprising the other stent constituting member 4b.

Each tubular-body forming elements 5a and 5b, formed in the each stent constituting members 4a and 4b, respectively, abutted each other as described above are abutted to each other so as to be alternately arranged to up-and-down direction as indicated by arrows $Y_1$ and $Y_2$, as shown in FIGS. 1 and 2. The tubular-body forming elements 5a and 5b abutted to each other make up a single tubular segment 6.

The paired stent constituting members 4a and 4b abutted to each other are combined together by joining the neighboring sides 8a and 11a of which the yarn 3 bent in a zigzag design, are abutted in parallel each other, to constitute a single tubular body 2.

Figure 8:
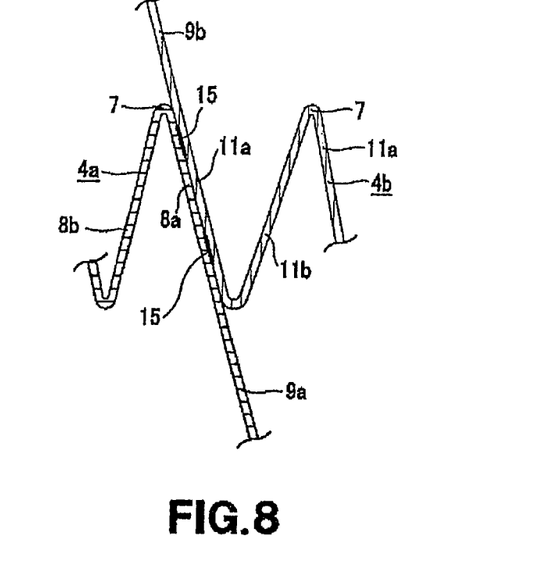
FIG. 8 is a partial plan view showing an example of yarns bent in a zigzag design, of which sides neighboring together that are abutted together in parallel are joined.

Each sides 8a and 11a may be joined with an adhesive. Joining with the adhesive may be done by spot, as the part of the neighboring sides 8a and 11a join spot 15, as shown in FIG. 8.

The sides 8a and 11a may also be joined with a solvent to dissolve a biodegradable polymer composing the yarn 3. That is, part of the sides 8a and 11a formed of a biodegradable polymer is dissolved and joined with a solvent. If the yarn 3 is formed of polylactic acid (PLLA), 1•4-dioxane is used as the solvent.

Further, the sides 8a and 11a may also be joined by using a solution of the biodegradable polymer obtained on dissolution with a solvent. The biodegradable polymer used here is the same kind of material as of the yarn 3. In case the yarn 3 is formed of polylactic acid (PLLA), the solution obtained on dissolving polylactic acid with a solvent 1•4-dioxane is used.

Furthermore, the sides 8a and 11a may also be joined by dissolving part of the sides 8a and 11a of the yarn 3 of a biodegradable polymer with the energy of the laser light radiated from a laser light source, such as laser diode.

Without regard to which sort of joining described above is used, part of the neighboring sides 8a and 11a may be joined by spot.

Figure 9:
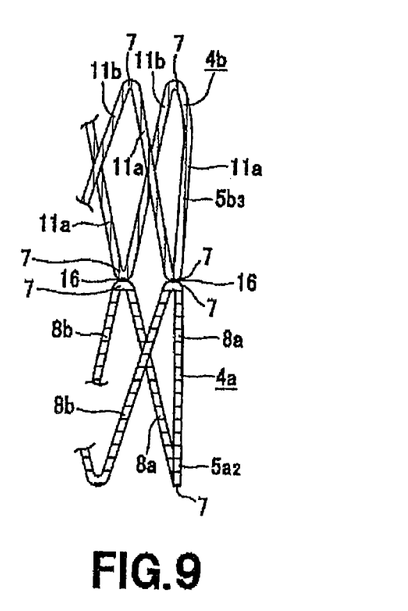
FIG. 9 is a perspective view showing an example of which apices of the bends of the yarn bent in a zigzag design joined together.

In the above embodiment, the paired stent constituting members 4a and 4b are combined together by joining the neighboring sides 8a and 11a which the yarn 3 bent in a zigzag design lies in parallel and abuts each other. Alternatively, the paired stent constituting members 4a and 4b may also be combined by joining the bends 7 facing and adjacent to one another of the yarn 3 bent in a zigzag design, as bond sites 16. In this case also, joining may be done by an adhesive, a solvent to dissolve a biodegradable polymer, or a solution of the biodegradable polymer obtained on dissolution with the solvent, or the method of dissolving part of the yarn 3 by heat energy of the laser light may be used. It is noted that only some proper parts of the bends may be joined rather than joining all bends 7 adjacent to each other. This aims to properly select the degree of flexibility of the stent for a vessel that displaces with the connecting parts 9 as flection point.

Joining the stent constituting members 4a and 4b may be both of the sides 8a and 11a adjacent to each other and the apices of the bends 7 with consideration of the size and the strength of the stent for a vessel being formed.

The tubular body 2, formed by abutting and joining a paired stent constituting members 4a and 4b, as described above, is made up by continuously combined tubular segments 6 in multistage, each of which is made up by abutting the tubular-body forming elements 5a and 5b of the stent constituting members 4a and 4b. The tubular segments 6 combined in multistage form may be flexed freely with the connecting parts 9a and 9b extended from the tubular-body forming elements 5a and 5b, combining those tubular segments 6, as displacing portions. That is, the tubular body 2 may be flexed freely to the direction of arrow X, orthogonalizing to the axial direction of arrows $Y_1$ and $Y_2$ in FIG. 1 of tubular segments 6 combined in multistage form.

Since the tubular body 2 of the present embodiment is comprised with a paired stent constituting members 4a and 4b exhibiting left-and-right symmetry, each tubular segments 6 are combined by the paired connecting parts 9a and 9b arranged at opposite positions by approximately 180°. Hence, the multistage-combined tubular segments 6 may be flexed with a paired connecting parts 9a and 9b staggered their positions each other by approximately 180°, as displacing portions. Since the tubular segment 6 of above and below are flexed, at this time, with a paired connecting parts 9a and 9b staggered their positions each other by approximately 180°, as displacing portions, each of these tubular segment 6 may be flexed to the direction of arrow X in FIG. 1 without generating significant displacement.

Moreover, the stent for a vessel 1 comprised with the tubular body 2 according to the present invention may be introduced into a sinuous vessel such as blood vessel with good conformability because the tubular segments 6 combined in multistage form is able to freely flex in the longitudinal direction, with a paired connecting parts 9a and 9b as displacing portions. That is, the stent for a vessel 1 according to the present invention is superior in flexibility.

Additionally, the tubular-body forming elements 5a and 5b provided in the stent constituting members 4a and 4b are formed by bending a single yarn 3 in a zigzag design, with uniform opening angles of $\theta_1$ and $\theta_2$. Hence, each sides 8a and 8b, and 11a and 11b combining the tubular-body forming elements 5a and 5b, are slanted at the opening angles of $\theta_1$ and $\theta_2$ toward the combining directions of the tubular-body forming elements 5a and 5b, respectively. Therefore, the sides 8a and 11a joining the tubular-body forming elements 5a and 5b in the stent constituting members 4a and 4b abutted each other, respectively continue while including toward the direction of $Y_1$ and $Y_2$ in the FIG. 1, respectively, which are the axial directions of the tubular body 2. That is, the join sites combining a paired tubular-body forming elements 5a and 5b that make up one tubular segment 6 are continued spirally as the locations of the join sites are staggered along the circumference of the tubular body 2. The tubular body 2, in which the join sites of each sides 8a and 11a are continued spirally may have uniform strength at any axial positions and may positively keep its cylindrical configuration. The stent for a vessel 1 formed with this tubular body 2 may reliably and uniformly support the inner wall of the vascular vessel such as a blood vessel in an expanded state, when it is introduced into the vessel.

The above embodiment described that, the tubular body 2 is formed by combining a paired stent constituting members 4a and 4b exhibiting left-and-right symmetry. The stent for a vessel according to the present invention may also be formed by combining three or more stent constituting members. For example, the tubular-body may also be constituted by combining three stent constituting members each having multistage tubular-body forming elements tierced a tubular segment. The tubular body may also be constituted by combining four stent constituting members each having multistage tubular-body forming elements quadrisected a tubular segment. These tubular-body forming elements in the stent constituting members are also formed with their positions staggered in circumferential to each stage direction, and the join sites joining the tubular-body forming elements are continued spirally continuously with their positions staggered along the circumference of the tubular body.

In case a tubular body is constituted by combining three stent constituting members which are combined the tubular-body forming elements in multistage form divided a tubular segment into three, each tubular-body forming elements of above and below are combined with their positions staggered by approximately 120° along the circumference of the tubular body to constitute the tubular body.

In case a tubular body is constituted by combining four stent constituting members which are combined the tubular-body forming elements in multistage form divided a tubular segment into four, each tubular-body forming elements of above and below are combined with their positions staggered by approximately 90° along the circumference of the tubular body to constitute the tubular body.

Plural stent constituting members making up the stent for a vessel according to the present invention may be formed with yarns of a biodegradable polymer made of different materials, not limited only to yarns of biodegradable polymer mode of the same material.

In addition, since the stent for a vessel 1 according to the present invention is constituted with a yarn of a biodegradable polymer, a drug may be contained easily. For example, a solvent with a drug dissolved therein may be applied on the surface of the yarn 3 constituting the tubular body 2.

Furthermore, since the stent for a vessel 1 according to the present invention is constituted with plural stent constituting members, different drugs may be contained in the respective stent constituting members 4a and 4b. In this case as well, a solvent with a drug dissolved in may then be applied on the surface of the yarn 3 constituting the respective stent constituting members 4a and 4b.

The stent for a vessel 1 according to the present invention, thus containing the drug, may also be used as a device for supplying the drug in the living body. In case the stent for a vessel 1 is constituted with plural stent constituting members 4a and 4b, plural sorts of drugs may be contained with ease and hence the stent may be used for administering a wide variety of drugs.

The present invention is not limited to the above embodiments described with reference to the drawings, and, as may be apparent to those skilled in the art, various changes displacement or substitution by equivalents may be attempted without departing from the scope and purpose of the invention.

INDUSTRIAL UTILIZABILITY

The stent for a vessel according to the present invention is implanted in a vessel of a living body, such as blood vessel of coronary artery, trachea or biliary and uses as a member for supporting the vessel from its inside. The stent for a vessel using a yarn of a biodegradable polymer disappears in the living body after lapse of a preset time after implanted in the vessel of a living body.

The invention claimed is:

1. A stent for a vessel comprising:
   a tubular body including a plurality of stent constituting members each formed by a single piece of yarn,
   wherein each of the plurality of stent constituting members comprises a tubular-body forming element formed by combining a plurality of tubular-body forming sub-elements each corresponding to a single stage via connecting parts, said tubular-body forming element being formed by bending the single piece of yarn in a zigzag design,
   wherein for each stage, said tubular-body forming sub-elements of different stent-constituting members are combined together such that they face each other and are abutted together in parallel to form a tubular segment corresponding to said stage, said tubular segment being constituted by continuously joining at least neighboring sides of each tubular-body forming sub-element together at a join spot,
   wherein said tubular body is formed by combining tubular segments in multistage form,
   wherein said yarn is formed of one or more biodegradable polymers selected from the group consisting of: polylactic acid (PLLA), polyglycolic acid (PGA), a copolymer of polyglycolic acid and polylactic acid, polydioxanone, a copolymer of trimethylene carbonate and glycolid, and a copolymer of polyglycolic acid or polylactic acid and s-caprolactone,
   wherein said tubular body is contracted or expanded in diameter with bends which simply touch each other without overlapping of said yarn bent in a zigzag design as displacing portions, and
   wherein said join spot includes an adhesive or a partially dissolved portion of said yarn.

2. The stent for a vessel according to claim 1, wherein said tubular body is formed by joining apices of neighboring bends of a yarn which contact each other without overlapping in a zigzag design.

3. The stent for a vessel according to claim 1, wherein said stent constituting members are formed so as to be symmetrical relative to one another.

4. The stent for a vessel according to claim 1, wherein for each tubular body forming element comprising a stent constituting member, the plurality of tubular body-forming sub elements are each formed with staggered angles by any of approximately 180°, 120° or 90° to a circumferential direction of said tubular body.

5. The stent for a vessel according to claim 1, wherein said tubular body is flexed to the substantially orthogonal direction to the longitudinal direction that said tubular-body forming sub-elements are combined in multistage, with connecting parts combining said tubular-body forming sub-elements of each stent constituting member in multistage as displacing portions.

6. The stent for a vessel according to claim 1, wherein the connecting parts which combine each tubular-body forming sub-element in multistage are staggered along a circumferential direction of said tubular body.

7. The stent for a vessel according to claim 1, wherein said yarn is a non-interrupted continuous monofilament.

8. The stent for a vessel according to claim 1, wherein said yarn is a multifilament made up of a plurality of monofilaments unified together.

9. The stent for a vessel according to claim 1, wherein said a plurality of stent constituting members are formed with yarns made of different biodegradable polymers.

10. The stent for a vessel according to claim 1, wherein said tubular body contains a drug.

11. The stent for a vessel according to claim 1, wherein each of said a plurality of stent constituting members contain different sorts of drugs.

12. The stent for a vessel according to claim 1, wherein said neighboring sides of each tubular-body forming sub-element are joined by partially dissolving said yarn using any one of a solvent for dissolving a biodegradable polymer, a solution obtained on dissolving a biodegradable polymer with a solvent or laser light energy.

* * * * *